United States Patent [19]

McCarthy et al.

[11] 4,086,344
[45] Apr. 25, 1978

[54] N,15-DIDEHYDRO-15-DEOXO-3,15-EPI(ME-THANO(ALKYLIMINO))RIFAMYCINS AND ANTIMICROBIAL COMPOSITIONS AND METHODS EMPLOYING THEM

[75] Inventors: James R. McCarthy; Jimmie L. Moore, both of Midland, Mich.

[73] Assignee: The Dow Chemical Company, Midland, Mich.

[21] Appl. No.: 722,455

[22] Filed: Sep. 13, 1976

[51] Int. Cl.² ............................................ A61K 31/505
[52] U.S. Cl. ................................ 424/251; 260/251 Q; 260/251 A
[58] Field of Search ....................... 260/251 A, 251 Q

[56] References Cited

U.S. PATENT DOCUMENTS 3,761,468  9/1973  Maggi ................................. 260/239

OTHER PUBLICATIONS

Kump et al., Helv. Chim. Acta, vol. 56, No. 7, pp. 2348–2353, 2360–2362 & 2375–2377 (1973).

*Primary Examiner*—R. J. Gallagher
*Assistant Examiner*—Diana G. Rivers
*Attorney, Agent, or Firm*—Daniel L. DeJoseph; C. Kenneth Bjork

[57] ABSTRACT

N,15-Didehydro-15-deoxo-3,15-epi(methano(alkylimino))rifamycins which can exist in either the quinone or hydroquinone form, are prepared from the corresponding Mannich base derivatives by an acid-catalyzed dehydration reaction.

6 Claims, No Drawings

N,15-DIDEHYDRO-15-DEOXO-3,15-EPI(METHANO(ALKYLIMINO))RIFAMYCINS AND ANTIMICROBIAL COMPOSITIONS AND METHODS EMPLOYING THEM

SUMMARY OF THE INVENTION

A new structural class of rifamycin antibiotics which have antitubercular and antibacterial utility are prepared from the corresponding Mannich base derivatives, 3 below, by an acid-catalyzed dehydration reaction pursuant to the following equation:

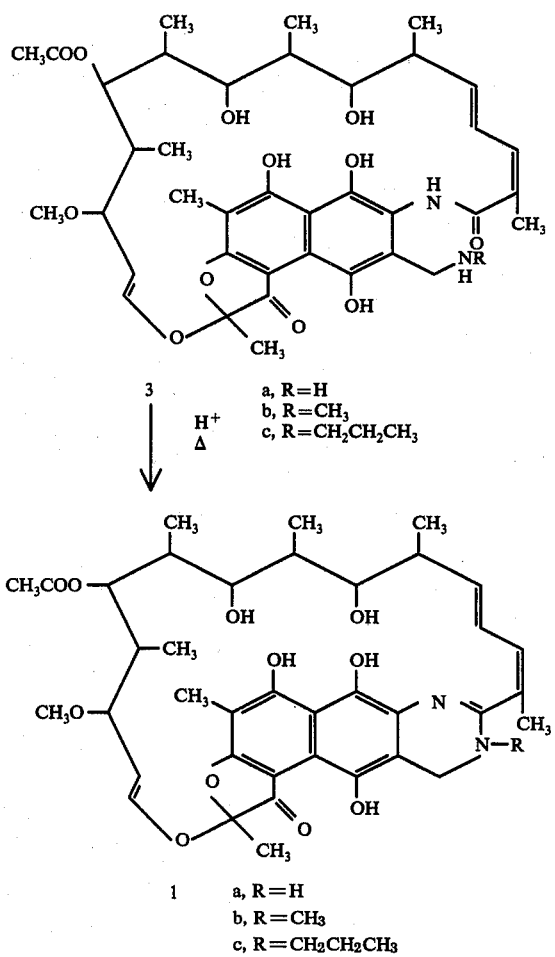

The product 1 can readily be oxidized to the following quinone from 2 with basic potassium ferricyanide.

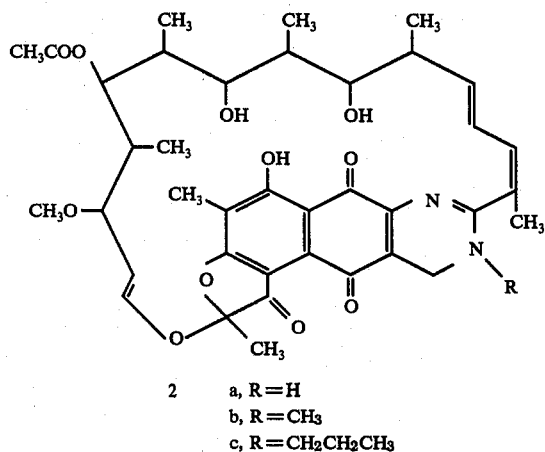

The Mannich base need not be isolated but can be prepared in situ from rifaldehyde by a new method using the appropriate amine, $NH_3$ (R=H) or $RNH_2$ (R=$CH_3$ or $CH_2CH_2CH_3$), hydrogen chloride and sodium cyanoborohydride. If the reaction with rifaldehyde is allowed to proceed for an extended period of time, the acid present in the reaction mixture will catalyze the ring closure leading to the desired product 1.

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

In the following examples, melting points were determined on a Thomas Hoover capillary melting point apparatus and are uncorrected. UV spectra were run on a Beckman Model 25 Spectrophotometer. NMR spectra were run on either a Varian T-60 or a Perkin-Elmer R-32. Thin layer chromatography (tlc) was run on glass plates coated with silica gel (Quantum Industries — Q1F). All chromatograms were run using the following solvent systems (SS): (1) upper phase of ethyl acetate:n-propanol:-water (4:1:2), (2) chloroform:ethyl acetate (98:2), (3) chloroform:methanol (95:5), (4) chloroform:methanol (9:1), (5) chloroform:acetone (1:1), (6) chloroform:methanol (98:2), (7) methanol, (8) acetone, (9) methylene chloride:acetone (95:5), (10) chloroform:methanol (8:2), hereinafter (SS 1 etc.). All evaporations were accomplished under reduced pressure using a Buchler rotating evaporator unless otherwise specified.

EXAMPLE 1

N,15-Didehydro-15-deoxo-3,15-epi(methano(methylimino)rifamycin SV (1b), Method 1

Reductive amination of 3-formylrifamycin SV (7.25 g, 10 mmol) with methylamine was performed as in the preparation of following Preparation A, Compound 3b, except the reaction time was increased to 16 hours. Tlc (SS 4) showed two products (both orange), $R_f$ 0.50 (minor component) $R_f$ 0.55 (major component). The crude product was chromatographed on 600 g of silica gel (Merck 60, 5 × 67 cm) using SS 4. The eluant was collected in 50 ml fractions and examined by tlc (SS 4). Fractions which contained only the main component were combined and concentrated to give 1.0 g of red-orange solid. The product was crystallized from reagent methanol to give 562 mg (0.78 mmol) of product 1b as bright orange crystals, ir (nujol): 3400, 1715, 1700, 1640 cm$^{-1}$; pmr (CDCl$_3$): δ 3.08 (S, 6H, OCH$_3$ and NCH$_3$), δ 2.08 (S, 6H, 14-CH$_3$ and acetate CH$_3$), δ 1.97 (S, 3H, 30-CH$_3$). UV (MeOH) max 271 nm (ε 12,700), 282 nm (12,590), 317 nm (16,600), 374 nm (9,400), 457 nm (16,200).

Calc'd for $C_{39}H_{50}N_2O_{11}$: C, 64.80; H, 6.97; N, 3.88. Found: C, 64.90; H, 7.00; N, 4.12.

EXAMPLE 2

N,15-Didehydro-15-deoxo-3,15-epi(methano(methylimino))rifamycin SV (1b), Method 2 Cyclizing of (3b) to (1b)

After standing several days, a CDCl$_3$ solution of preparation 3b was examined by tlc (SS 4), which showed one orange spot ($R_f$ 0.55) and showed that the new material was identical to product 1b. Likewise, a chloroform solution of preparation 3b, which remained tightly capped in a vial for several days, was converted to product 1b, according to tlc.

EXAMPLE 3

N,15-Didehydro-15-deoxo-3,15-epi(methano(imino))-rifamycin SV (1a)

To a dry 250 ml 3-neck round bottom flask under a nitrogen atmosphere was added 60 ml of methanolic ammonia (3.4 g $NH_3$) (200 mmoles) and 33 ml of 3 N methanolic hydrogen chloride (100 mmoles) with cooling. The mixture was treated with 14.5 g (20 mmoles) of rifaldehyde and 900 mg (16 mmoles) of sodium cyanoborohydride. The reaction was stirred overnight at room temperature, poured into 100 ml of 10% aqueous ascorbic acid and extracted with ethyl acetate (2 × 150 ml). The combined organic layer was dried ($Na_2SO_4$) and evaporated to dryness. The resulting solid was chromatographed on 600 g of silica gel (Merck 60, 5 × 65 cm) initially using chloroform:methanol (9:1). As soon as colored material started to elute from the column, fractions were collected as follows:

| Fraction No. | Volume (ml) | $CHCl_3$/MeOH Ratio |
| --- | --- | --- |
| 1 | 250 | 9:1 |
| 2 | 250 | 9:1 |
| 3 | 150 | 9:1 |
| 4 – 8 | 1200 | 9:1 |
| 9 – 11 | 900 | 9:1 |
| 12 – 14 | 550 | 1:1 |
| 15 – 17 | 700 | 1:1 |

Fraction 2 was homogenous by tlc (SS 10) $R_f$0.91 and was concentrated in vacuo yielding 0.55 g of an orange-red solid, 1a. The product can be crystallized from methanol. This material has the same characteristic UV absorption spectrum as product 1b: UV (MeOH) max 267, 277, 316, 371 and 453 nm; ir (nujol) 3400, 3150, 1735 (shoulder), 1720, 1650, 1640, and 1620 cm$^{-1}$; nmr (DMSO-$d_6$-CDCl$_3$) δ 9.7 (broad S, 1, amidine NH), 4.57 (S, 2, C$\underline{H}_2$NH), 3.0 (S, 3, OCH$_3$); 2.08 (S, 3, 14 CH$_3$), 2.0 (S, 3, acetate), 1.95 (S, 3, 30 CH$_3$), 1.65 (S, 3, 13 CH$_3$), 0.95, 0.85 and 0.67 (3doublets, 9, each d has J=7Hz, 3 ansa CH$_3$).

EXAMPLE 4

N,15-Didehydro-15-deoxo-3,15-epi(methano(imino))-rifamycin SV (1a), Method 2

A 1.18 g (1.62 mmol) quantity of 3-aminomethylrifamycin SV, preparation 3a, and 3 drops of glacial acetic acid were dissolved in 100 ml of 1,2-dichloroethane. The solution was stirred and heated, and bright orange crystals began to appear after a short period of time. After refluxing overnight, the reaction mixture became homogeneous. Tlc (SS 4) showed that the solution contained the cyclic product ($R_f$0.5) and various impurities. The solution was allowed to cool, then concentrated to a dark solid. The residue was dissolved in the minimal amount of chloroform-methanol (90:10) and applied to a column of silica gel (75 g, Baker 60-200 mesh) packed with the same solvent pair. The column was eluted with SS 4 and the eluant was collected in 50 ml fractions. The fractions were examined by tlc (SS 4). Fractions containing the pure product were combined and concentrated to give 0.6 g (0.85 mmol, 52%) of the cyclic derivative 1a.

EXAMPLE 5

N,15-Didehydro-15-deoxo-3,15-epi(methano(imino))-rifamycin S (2a)

A 1.20 g (1.69 mmol) quantity of the hydroquinone form of compound 1a was dissolved in 100 ml of reagent chloroform and was washed thoroughly with aqueous $K_3Fe(CN)_6$ (3.0 g in 150 ml). The chloroform layer was dried ($Na_2SO_4$), filtered, and concentrated to dryness. A concentrate of the residue in chloroform-methanol (98:2) was passed through 30 g of silica gel (Woelm, 70–230 mesh) using the same solvent pair. The filtrate was concentrated to dryness and the residue was crystallized from anhydrous ether. The crystals were filtered, washed with a small volume of ether, and dried (vacuum) to give 413 mg (0.58 mmol, 34%) of the quinone 2a as fine green crystals, homogenous by tlc: $R_f$0.74 (SS 4); ir (nujol): 3400, 3375, 3300, 1735, 1720, 1640, 1600 cm$^{-1}$, pmr (CDCl$_3$): δ 12.3 (very broad S, 1H, exch. with $D_2O$, phenolic OH), δ 5.7-6.7 (m, 4H), δ 5.10 (dd, $J_{27,28}$=8, $J_{28,29}$=12.5, 1H, 28-H), δ 4.90 (d, J=19, 1H, Ar—C$\underline{H}_2$—NH—), δ 4.80 (d, J=10, 25-H), δ 4.33 (d, J=19, 1H, Ar-C$\underline{H}_2$-NH), δ 3.10 (S, 3H, OCH$_3$), δ 2.30 (S, 3H, 14-CH$_3$), δ 2.04 (S, 6H, 30-CH$_3$ and 36-CH$_3$), δ 1.70 (S, 3H, 13-CH$_3$), δ 0.50 1.0 (3d, J=7, each 3H, 31-CH$_3$, 32-CH$_3$, 33-CH$_3$), δ 0.22 (d, J=7, 3H, 34-CH$_3$); UV-VIS(CH$_3$OH): $\lambda_{max}$272 nm (ε 17,400), sh 303 nm (ε 14,100), 375 nm (ε 7,300), 439 nm (ε 8,000).

Calc'd for $C_{38}H_{46}N_2O_{11}$: C, 64,57; H, 6.56; N, 3.96. Found: C, 64.29; H, 6.70; N, 3.81.

EXAMPLE 6

N,15-Didehydro-15-deoxo-3,15-epi(methano(n-propylimino))rifamycin SV (1c)

To a solution of 3.54 g (60 mmoles) of dry n-propylamine (distilled from CaH$_2$), 25 ml of dry methanol, and 4 ml of 5 N methanolic hydrogen chloride (20 mmoles) was added 7.25 g (10 mmoles) of rifaldehyde and 450 mg (7 mmoles) of sodium cyanoborohydride. The reaction was allowed to run 25 days at room temperature under a N$_2$ atmosphere and then poured into 50 ml of 10% aqueous ascorbic acid, extracted with ethyl acetate (2 × 75 ml) and the combined organic layer was washed with NaCl brine (50 ml), dried (Na$_2$SO$_4$), and evaporated to dryness. The concentrate was chromatographed on silica gel (750 g, 80 × 5 cm) using CHCl$_3$:MeOH (19:1). As soon as colored material started to elute from the column, fractions were collected as follows:

| Fraction No. | Volume (Ml) |
| --- | --- |
| 1 | 200 |
| 2 | 200 |
| 3 | 200 |
| 4 – 6 | 1000 |
| 7 | 500 |
| 8 – 10 | 1000 |
| 11 | 300 |

Fractions 2, 4–6, and 8–10 contained three different components and were homogenous by tlc; $R_f$ values were as follows:

| Fraction No. | $R_f$ Value in Solvent | |
|---|---|---|
| | SS 4 | SS 3 |
| 2 | 0.82 | 0.5 |
| 4-6 | 0.77 | 0.4 |
| 8 - 10 | 0.69 | 0.33 |

Each set of fractions was combined and evaporated to dryness. Fraction 4-6 was triturated with ether and the resulting solid (6 g) of 3-propylaminomethylrifamycin SV, preparation 3c, was collected by filtration. Fraction 8-10 (1.2 g) was crystallized from ca. 10 ml of ethyl acetate to yield 300 mg of desired crystalline product, 1c, mp 184°-7° C (dec.). A small sample of product 1c was recrystallized from ethyl acetate for analysis, UV (MeOH) max 268, 281, 316, 375, and 454 nm ($\epsilon$ 13,800, 13,650, 17,700, 8,600, and 17,000).

Anal. Calc'd for $C_{41}H_{54}N_2O_{11}\cdot H_2O$: C, 64.04; H, 7.34; N, 3.64. Found: C, 64.07; H, 7.38; N, 4.05.

Preparation A

Preparation of the Mannich Base, 3-Methylaminomethylrifamycin SV (3b)

An 11.3 ml (60 mmol) quantity of 5.3 M methanolic methylamine (anhydrous) was added to 75 ml of absolute methanol. To this stirred solution was added 4 ml (20 mmol) of 5 M methanolic HCl, followed by 7.25 g (10 mmol) of 3-formylrifamycin SV. Sodium cyanoborohydride (684 mg, 10 mmol) was added and the solution was stirred for 3 hours at room temperature. The reaction was poured into 100 ml of 10% aqueous ascorbic acid, diluted with 300 ml of water and 300 ml of brine, and extracted with ethyl acetate (4 × 200 ml). The extracts were dried ($Na_2SO_4$), filtered, and concentrated to give a dark solid. Examination of the solid by tlc (SS 4) showed that no rifaldehyde was present, and showed two products (both orange), $R_f$ 0.55 (minor component) and $R_f$ 0.50 (major component). The solid was chromatographed on 700 g of silica gel (Merck 60, 5 × 80 cm) using SS 4. The eluant was collected in 200 ml fractions and examined by tlc (SS 4). Fractions which contained only the main component were combined and concentrated to give 2.3 g of red-orange solid. The product was crystallized from reagent ethyl acetate to give 1.53 g (2.06 mmol) of 3-methylaminomethylrifamycin SV (3b) as bright orange crystals, ir (nujol): 3425, 3300, 3135, 1715, 1700, 1640 cm$^{-1}$; pmr ($CDCl_3$): $\delta$ 2.93 (S, 3H, $NCH_3$). A small sample of the crystalline product was dried under high vacuum (1 mm, 40° C) for 72 hours to provide an analytical sample.

Calc'd for $C_{39}H_{52}N_2O_{12}\cdot CH_3CO_2C_2H_5$: C, 62.30; H, 7.29; N, 3.38. Found: C, 62.20; H, 7.26; N, 3.37. UV (MeOH): 314 nm ($\epsilon$ 17,400), 447 nm ($\epsilon$ 13,350).

The compounds of this invention have antimicrobial activity, and, in practice, are useful in combination with conventional pharmaceutical carriers. Thereby, the active compounds may be applied directly or indirectly to the microorganisms which it is desired to control. In in vitro agar Petri dish dilution tests as conventionally carried out for determining bactericidal utility, the minimum inhibitory concentration (MIC) in parts per million for Compound 1b, R = $CH_3$, was 0.2 for S. aureus ATCC 6538, 0.8 for S. aureus Tour, >100 for S. aureus Tour RAMP/R, 3 for S. haemolyticus C 203, 25 for S. faecalis, 3 for D. pneumoniae UC 41, >$\phi$ for P. vulgaris X 19 H, >100 for E. coli, >100 for K. pneumoniae, 100 for P. aeruginosa and 1.2 for M. tuberculosis. For Compound 1a, R = H, the MIC for S. marscesens was 100 and for S. aureus 6538 was 50.

What is claimed is:

1. A compound which, in the hydroquinone form, is represented by the formula

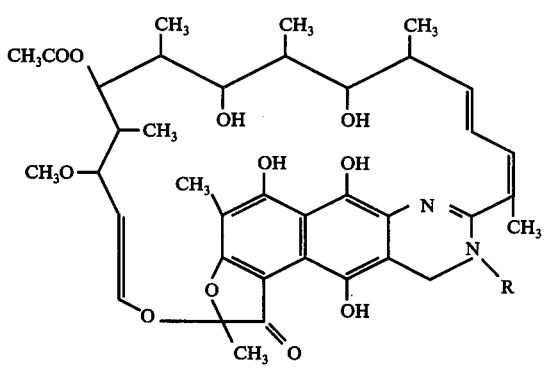

and, in the quinone form, is represented by the formula

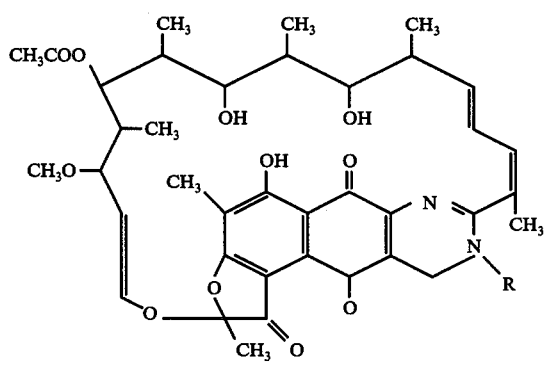

wherein R represents H, $CH_3$ or n-propyl.

2. The compound of claim 1 wherein R represents H.

3. The compound of claim 1 wherein R represents $CH_3$.

4. The compound of claim 1 wherein R represents n-propyl.

5. An antimicrobial method wherein an antimicrobially-effective amount of a compound as claimed in claim 1 is applied to a microorganism or to the habitat of said microorganism.

6. An antimicrobial composition comprising an antimicrobial amount of a compound as claimed in claim 1 in combination with a pharmaceutical carrier.

* * * * *

UNITED STATES PATENT OFFICE
CERTIFICATE OF CORRECTION

Patent No. 4,086,344         Dated April 25, 1978

Inventor(s) James R. McCarthy et al.

It is certified that error appears in the above-identified patent and that said Letters Patent are hereby corrected as shown below:

Column 1, line 52 "from 2" should read -- form 2 --;

Column 4, line 19 "2as" should read -- <u>2a</u> --;

Column 6, line 5 " >∅ for P. vulgaris" should read -- >100 for P. vulgaris --;

Column 6, between lines 30 and 45 "Formula" should read as follows:

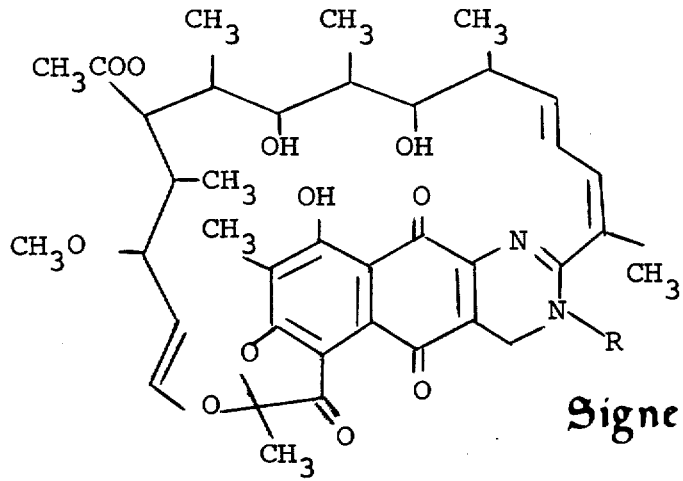

Signed and Sealed this

Tenth Day of October 1978

[SEAL]

Attest:

RUTH C. MASON
Attesting Officer

DONALD W. BANNER
Commissioner of Patents and Trademarks